US007521224B2

(12) United States Patent
Johnson et al.

(10) Patent No.: US 7,521,224 B2
(45) Date of Patent: Apr. 21, 2009

(54) MICROELECTRONIC CELL ELECTROPORATION ARRAY

(75) Inventors: Lee Johnson, Baltimore, MD (US); Dean Scribner, Arlington, VA (US); Joseph Pancrazio, Germantown, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 673 days.

(21) Appl. No.: 10/673,352

(22) Filed: Sep. 30, 2003

(65) Prior Publication Data

US 2005/0070018 A1    Mar. 31, 2005

(51) Int. Cl.
*C12M 1/42* (2006.01)
*C12M 3/00* (2006.01)
*C12N 15/87* (2006.01)
*C12N 13/00* (2006.01)

(52) U.S. Cl. .................. 435/285.2; 435/817; 435/461; 435/470; 435/173.1; 435/173.4; 435/173.5; 435/173.6; 435/288.3; 435/288.4; 435/288.5; 435/288.7

(58) Field of Classification Search .............. 435/285.2, 435/817, 461, 470, 173.1, 173.4, 173.5, 173.6, 435/288.3, 288.4, 288.5, 288.7
See application file for complete search history.

(56) References Cited

U.S. PATENT DOCUMENTS

| 5,676,646 | A | 10/1997 | Hofmann et al. |
| 6,027,488 | A | 2/2000 | Hofmann et al. |
| 6,103,084 | A | 8/2000 | Uhen |
| 6,352,853 | B1 | 3/2002 | King et al. |
| 6,393,327 | B1 | 5/2002 | Scribner |
| 6,451,002 | B1 | 9/2002 | Dev et al. |
| 2004/0197883 | A1 * | 10/2004 | Dzekunov et al. ......... 435/173.6 |
| 2004/0241965 | A1 * | 12/2004 | Merritt et al. ............... 438/478 |
| 2005/0054969 | A1 * | 3/2005 | Hoff et al. ..................... 604/20 |
| 2005/0112544 | A1 * | 5/2005 | Xu et al. ........................ 435/4 |
| 2006/0206161 | A1 * | 9/2006 | Nicolelis et al. .............. 607/45 |

* cited by examiner

*Primary Examiner*—William H Beisner
*Assistant Examiner*—Nathan A Bowers
(74) *Attorney, Agent, or Firm*—John J. Karasek; Kerry L. Broome; Rae Lynn P. Guest (57) ABSTRACT

The electroporation array is comprised of three technologies: microwire glass electrodes, microelectronic multiplexer stimulator chips and microfluidic flow chamber. Various substances, such as genes, gene silencing RNAi, gene inhibition agents or drugs, can be perfused into the microfluidic flow chamber. The entry of the various substances into the cells will be facilitated by electroporation. An applied electric potential causes nanoscale pores to open in the cell membrane allowing substances in the solution to freely diffuse into the cell. The specific cells selected for electroporation are defined using the computer controlled microelectronic stimulator array. An "image" of which electrodes within the array to apply the electric potential to, and thus electroporate, is de-multiplexed onto the array. All the selected electrodes deliver a current pulse varied by the intensity of the de-multiplexed "image". By serially perfusing different substances across the cells or tissue and electroporating different areas of the cell or tissue culture, it will be possible to have different cells within the culture contain different genes, gene silencing RNAi, gene inhibition agents, drugs, chemicals or other substances or sets thereof. It is also possible to re-electroporate subsets of cells on the array to allow for multiple gene combinations. In essence, this invention allows for the creation of cell arrays and would be analogous to gene arrays, which have been so important in recent advances in biotechnology, such as the human genome project.

16 Claims, 7 Drawing Sheets

MICROELECTRONIC CELL ELECTROPORATION ARRAY

BACKGROUND

The present invention deals generally with electroporation, specifically the concept of spatially targeted entry of genes, drugs, chemicals and other substances into cells with a microelectronic electroporation array.

Gene therapy is an experimental method that attempts to replace, manipulate, or supplement nonfunctional or malfunctioning genes in cells with other genes to cure disease. The disease is generally one in which the patient's version of the gene is significantly different from that found the general population. As a preliminary step in studying a candidate gene to be used for therapy, that gene may be inserted into cells of the type involved in the disease. If the candidate gene alleviates the cellular component of the disease it may be studied further in vivo in an animal model of the disease. In some cases it is not known what the exact difference in the disease gene is or even which gene within a chromosome is related to the disease. In this case, one could try to carefully modify the nucleotide base pairs in the gene, testing them in cells one by one until the cause of the disease is found. The problem is with the magnitude of the search: typically there are 1000 to 100,000 base pairs within a given gene. Another problem becoming more evident is the fact that most diseases are multifactorial or result from a number of gene "defects". Thus, one would have to study combinatorial nucleotide changes—theoretically this can become an astronomical number. What is clearly needed is a method to study the treatment of cells with large numbers of genes in a parallel or combinatorial manner.

The traditional method of study has been to serially introduce genes into cells. A separate experiment is required to study each new candidate gene. In addition, most current techniques for inserting genes into cells to study their benefit or detriment do not lend themselves to rapid parallel study. These gene insertion methods include, viral transfection, chemical weakening of the cell membrane and microinjection of the genes into individual cells. Electroporation is another method that is used to serially study gene effects.

Electroporation is the creation of nano-scale transient pores in the cell membrane with a relatively high electrical potential gradient. There are generally three existing methods for electroporating. The first is to use a chamber, or "well", with a pair of plate electrodes. A solution containing the cells to be electroporated is placed into the well and a voltage pulse is given across the electrode pair (Neumann, et al., 1982). The second method is to use a probe with a pair or more of electrodes at the tip that can be placed on the surface, subcutaneous or deep within a surgical field to electroporate cells in vivo, or in a patient (U.S. Pat. No. 6,451,002). A third method is for cells to be cultured on the surface of an electrode (Lin and Huang. 2001, Lin et al., 2001, Huang and Rubinsky. 1999) or brought in close approximation (Olofsson et al., 2003) to an electrode and electroporated in small groups or one at a time. The problem with the prior art in this field is the lack of a high-density electrode array for electroporating, a method to hold cells safely in contact with the array and a method to put a variety of genes in contact with the cells for electroporating. Our invention is a microelectronic electroporation array with over 3000 independent electrodes. This will allow for parallel study of the cellular effect of numerous genes, drugs or other substances.

One alternative to our invention is to use a multi-well plate, a disposable cell culture container with a number of separate "wells", 96 is a common number, to hold cell suspensions or solutions. Each well can be filled with cells in suspension and different genes in solution could be added to each well and electroplated with an electroporation array. Such a system has been described in U.S. Pat. No. 6,352,853 King. et al. The disadvantages compared to our invention are; a higher volume of costly gene or drug solution will be required, imaging all the cells at one time is difficult, large arrays with 3000 or more discrete experiment sites are difficult to design and use efficiently and it is not possible to study cells electroporated with different genes in one chamber.

A paper by Huang and Rubinsky (Huang and Rubinsky. 1999) describes an early version of the concept of single or few cell electroporation with low voltages. The device described is different from our invention in that there is only one electrode site. The cell to be electroporated flows in solution until it is trapped in a hole and electroporated.

A paper by Lin and Huang (Lin and Huang, 2001) demonstrates that low voltage electroporation of cells plated on electrodes can be performed. Unlike our invention, the "microchips" described in this paper are not the type that can be manufactured by the thousands for affordability using standard silicon wafer fabrication technologies. Furthermore, each chip contains only one or a few independent electrodes. Our device can be manufactured of silicon using standard methods. Our initial device uses on chip multiplexers to control 3200 independent electrode sites, much larger numbers of sites are possible. This allows for low cost, one-time use and thousands of experiments to be performed in parallel. Another paper by the same research group (Lin et al., 2001) is similar to the above paper. It describes a flow through version of the same device. Cells in solution are passed between two electrodes for electroporation. The device is different from our invention in that the cells are not stationary and there is only one electrode.

There are a number of electroporation devices that involve fluidics or fluid flow management. In the case of our invention, the fluid containing a drug or gene flows but the cells are fixed, other inventions are designed to have the cells suspended in the fluid (U.S. Pat. Nos. 5,676,646, 5,545,130, 5,507,724, 5,704,908, 6,027,488, 6,074,605, 6,090,617 6,485,961). Some of these devices are for in vivo use to treat blood cells with genes or drugs. The blood flows through the device or the device is inserted into the blood vessel. Some of these devices are used to pump fluid into non-vascular body cavities. Some of these devices are designed for flowing a cell suspension through an electroporation chamber. None of the above devices are for flowing different solutions carrying different genes, drugs etc for electroporation of stationary cells.

U.S. Pat. No. 6,393,327 (Scribner) describes the stimulation array used in the present invention. The previous patent does not describe the electroporation application, processes or additional technology required.

The voltages required to electroporate cells depend on the distance between the electrodes. A paper by Nolkrantz demonstrates a single cell, DC voltage electroporation system with required voltages to distance ratios (electric fields) of 137 V/cm with a 30 µm diameter source electrode and saline bath return electrode. They calculated a cellular transmembrane voltage of 206 mV for 5-second pulses. In general the lower the voltage to distance ratio the longer the required pulse duration. The reported transmembrane voltages required for 1 ms pulses are 200-300 mV (Ryttse et al), equivalent to 133-200 V/cm. For the present invention the absolute voltages required at the electrode surface would be less than 3V. The distance between adjacent unit cells (centerto-center) is 30 and 50 μm in the x and y directions. That would yield a voltage to distance ratio of at least 600V/cm or 1000 V/cm, more than sufficient for electroporation with 5 sec or 1 ms pulses durations. In the Nolkrantz report, the spread of electroporation was limited to the single cell being electroporated.

SUMMARY OF THE INVENTION

The objective of this invention is to allow for controlled entry of genes, drugs, chemicals or other substances into a few selected cells among many cells cultured on an array.

Another objective would be to use the microelectronic stimulator array to perform combinatorial studies of the roles of certain genes, drugs, chemicals or other substances in affecting cells in a positive or negative way. The positive or negative effect of the substances or genetic modifications could be viewed with optical imaging of markers for cell status and function.

Another objective is an electroporation array in which the extent of electroporation could be varied from one region of the cells to the other.

Another objective for the present invention would be the study of biologic or chemical agents. Biological or chemical agents expected to be hazardous could be perfused over the cells and their uptake into the cells accelerated or increased to allow the observation of the effect of low concentrations of the agents.

Still another objective of the present invention is the ability to study the interaction of cells electroporated with a variety of genes in one cell or tissue culture chamber.

These and other objectives are accomplished by the electroporation array comprising of three technologies: microwire glass electrodes, microelectronic multiplexer stimulator chips and microfluidic flow chamber. Various substances (genes, gene silencing RNAi, gene inhibition agents, drugs etc.) can be perfused into the microfluidic flow chamber. The entry of the various substances into the cells will be facilitated by electroporation. The specific cells selected for electroporation are defined using the computer controlled microelectronic stimulator array. An "image" of which electrodes within the array to stimulate is de-multiplexed onto the array. All the selected electrodes deliver a current pulse varied by the intensity of the demultiplexed "image". By serially perfusing different substances across the cells or tissue and electroporating different areas of the cell or tissue culture, it will be possible to have different cells within the culture contain different genes, gene silencing RNAi, gene inhibition agents, drugs, chemicals or other substances. In essence, this invention allows for the creation of cell arrays and would be analogous to gene arrays, which have been so important in recent advances in biotechnology, such as the human genome project.

The present invention will provide rapid parallel analysis of gene therapies. This would be achieved by electroporating a number of genes, gene silencing RNAi, or gene inhibition agents expected to improve cell function into known regions of the cell culture. A global injury or stress could be given to all the cells and the regional variation in the viability of the cells would indicate which genes, gene silencing RNAi, or gene inhibition agents were most useful. As with the set of genes, gene silencing RNAi, or gene inhibition agents described above, a set of drugs could be studied to determine their relative usefulness in fighting a specific disease or their potential side effects.

DETAILED DESCRIPTION OF THE INVENTION

Figure 1:
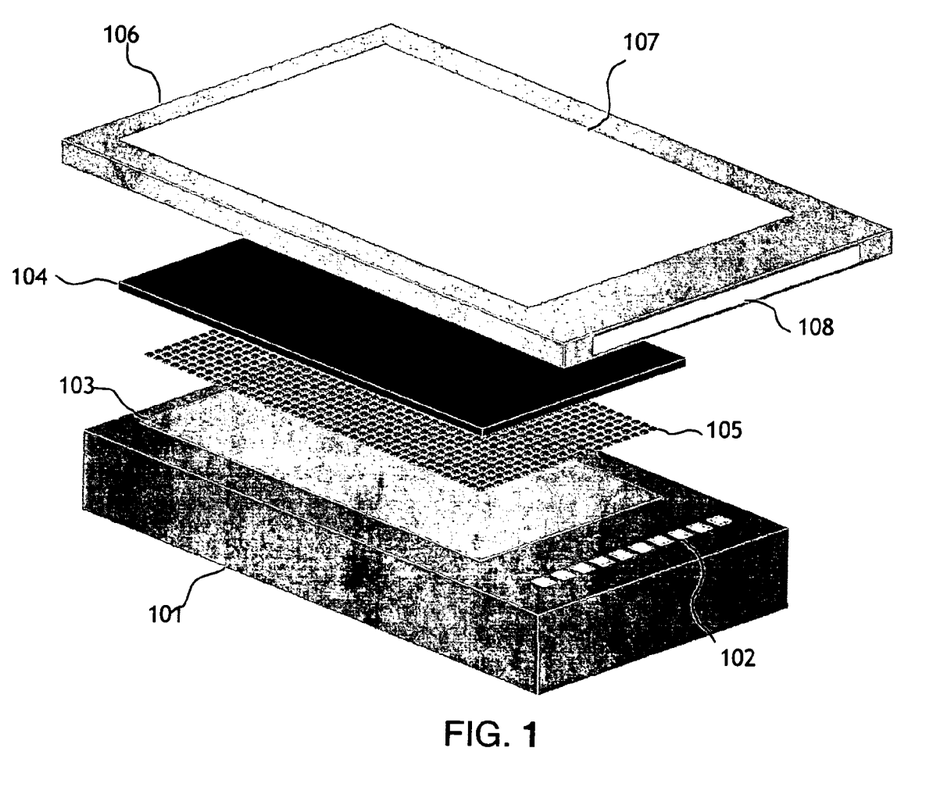
FIG. 1 shows the main components of the electroporation array.

The present invention, shown in FIG. 1, has 3 primary components; a microelectronic stimulator array 101, a conducting electrode material 104 onto which the cells or tissue are cultured and a fluid flow chamber 106 and apparatus to control the solutions of genes, gene silencing RNAi, gene inhibition agents, drugs or other substances to be presented for entry into the cells. The timing of the fluid flow and the active areas of the stimulator array will be controlled via a computer interface.

Microelectronic silicon stimulator array 101 has 10 bond pads 102, which are connected to the power supply, clocks, biases and data I/O. The chip also has an active area 103 that has a number of vias, which are connected to conducting electrode material 104 with indium bump bonds 105. Fluid flow chamber 106 has an optical window 107 on its top (that can be coated with a transparent electrode material, such as a thin metal layer) and inflow and outflow 108 on the sides.

Figure 2:
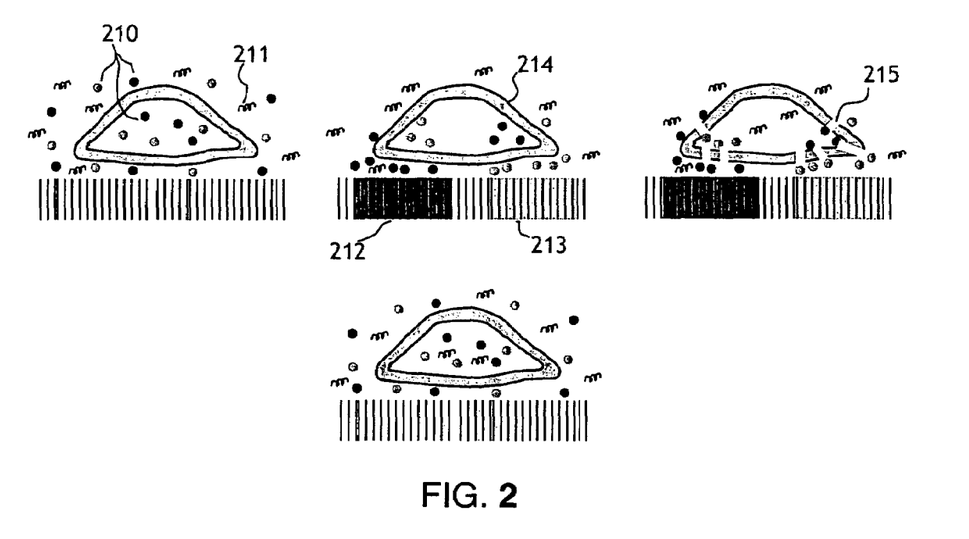
FIG. 2 shows the general process of electroporation of a cell cultured (grown) on the electrode surface.

FIG. 2 The electroporation process involves three phases. First the applied electric field across a cathode 212 and an anode 213 causes ions 210 within the cell to move and attract extracellular ions to a cell membrane 214. The large amplification of applied field at the cell membrane causes pore 215 formation and genes 211 or other substances can move into the cell via diffusion. Finally, the pores close shortly after the termination of the applied field leaving the genes or other substances inside the cell.

Figure 3:
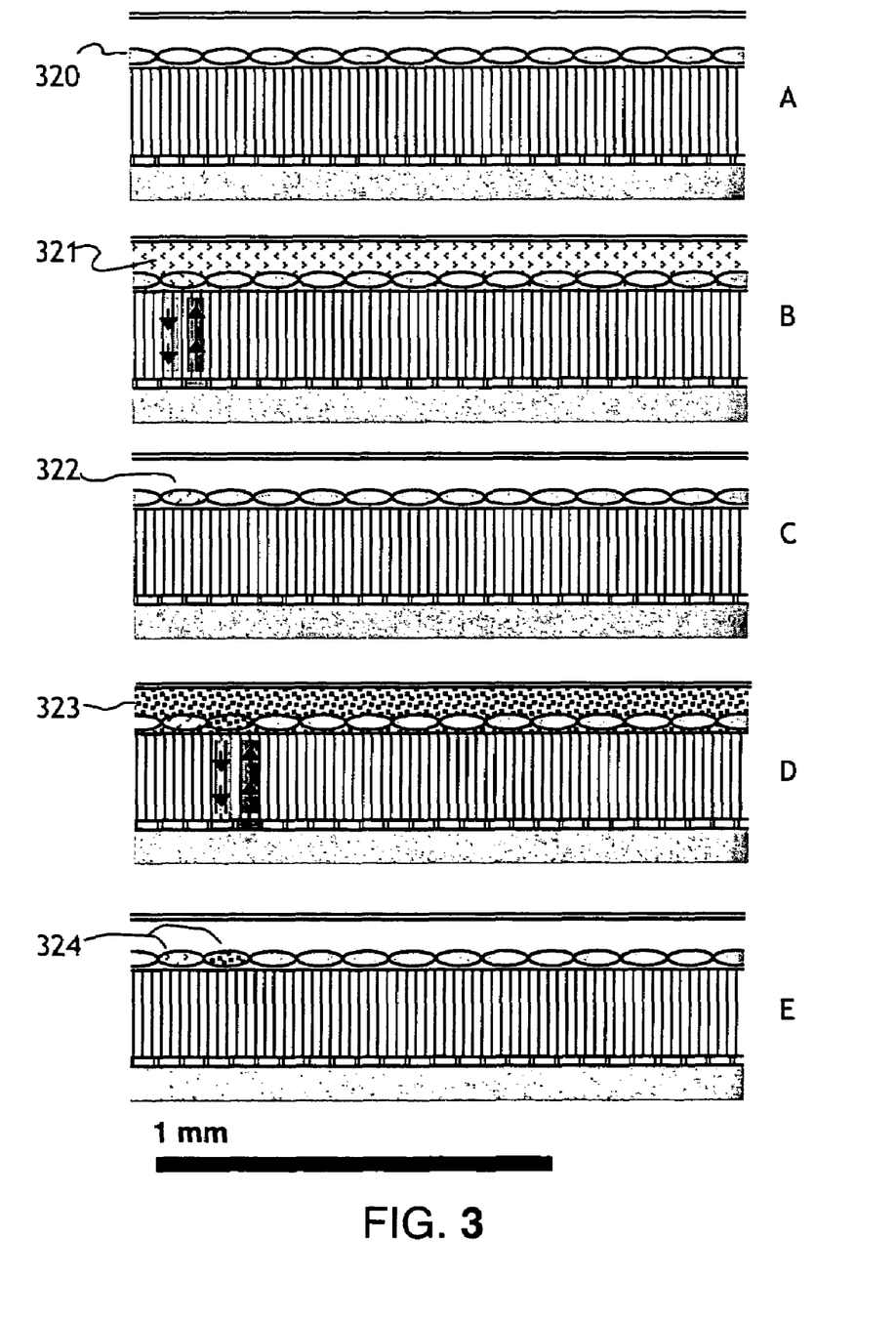
FIG. 3 shows the process of loading different substances in to different cells or cell groups using electroporation and washout of the substance.

Cell loading with the electroporation array is shown in FIG. 3. In frame A, the cells 320 are cultured on the surface of the array and surrounded by saline solution in a perfusion chamber. In frame B the first gene carrying solution 321 fills the chamber and the first region of the array is electroporated allowing the DNA to enter the cell(s) in that region. In frame C, the gene carrying solution has been washed out with normal saline solution and the DNA remains in the cell(s) 322. In frame D, the second gene solution 323 fills the chamber and the second region of the array is electroporated. In frame E, the second gene solution has been washed out and now two different genes, gene silencing RNAi, gene inhibition agents have been loaded into two different cells or cell groups 324. The process continues until all desired genes, gene silencing RNAi, gene inhibition agents or substances have been electroporated into the cells. For a 2-D array the process can be performed on a row-by-row and column-by-column basis for combinatorial experiments to examine the effects of two or more genes, gene silencing RNAi, gene inhibition agents per cell.

Stimulator Multiplexer

Figure 4:
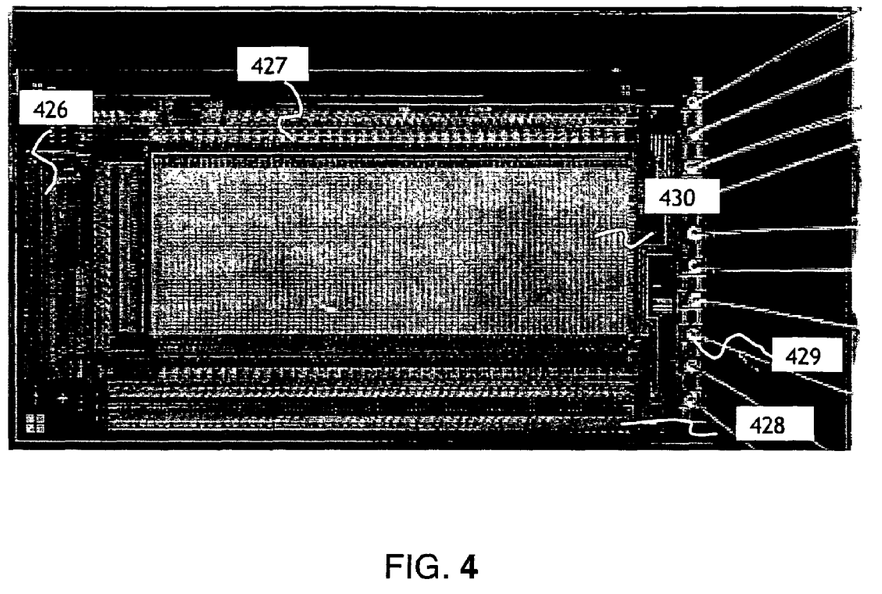
FIG. 4 shows a top view of the fabricated electroporation array microelectronic multiplexer.

The preferred embodiments of the microelectronic stimulator array and conducting electrode material have been described in U.S. Pat. No. 6,393,327B1. The 2-D multiplexer array of FIG. 4 is similar to infrared focal plane array (IRFPA) multiplexers that are microelectronic devices fabricated at silicon foundries. An IRFPA multiplexer is a 2-D array that reads out the infrared (IR) image captured by a complimentary detector array that converts photons into electrical charge. The charge is integrated and stored in each unit cell for a few milliseconds. The full image is then multiplexed off the array at frame rates compatible with commercial video. For an electroporation array the process is essentially reversed and the device acts as a de-multiplexer that obtains its input "image" of which electrodes to activate from a compute. That is, the electroporation array will perform a de-multiplexing operation, but will be referred to here simply as a multiplexer. The preferred embodiment of the stimulator multiplexer is imaged in FIG. 4. The stimulator chip contains circuits for reading in the stimulus pattern into the rows 426 and columns 427 of the array, reading out the stimulated voltages 428, bond pads 429 to connect to the external drive electronics and 3200 vias 430 to connect to the channel glass electrode.

Figure 5:
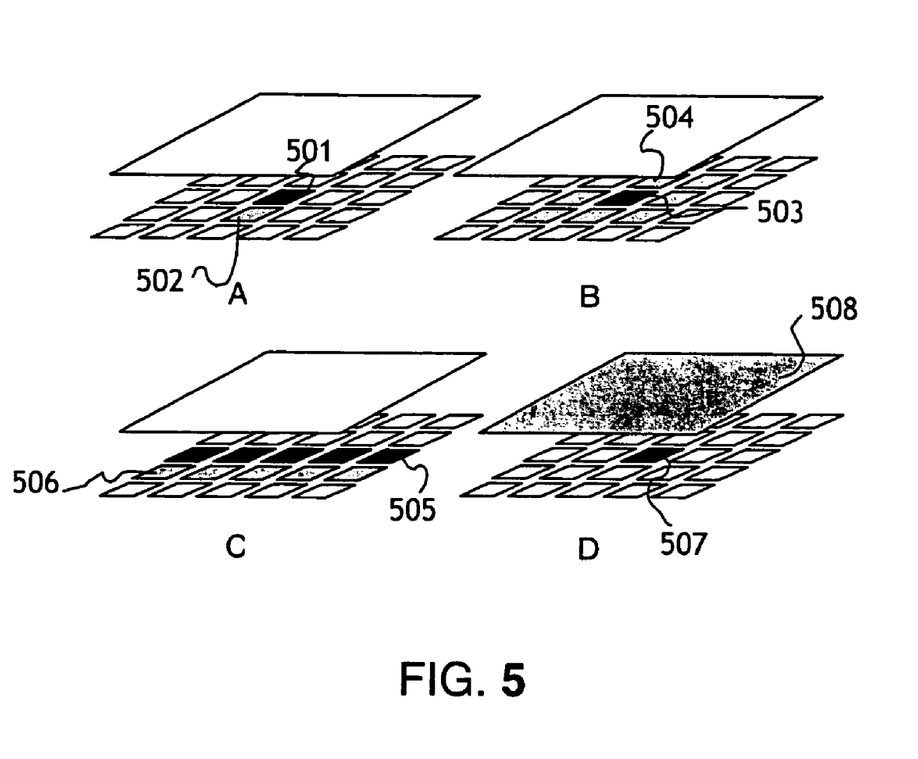
FIG. 5 shows four possible orientations of the electrode geometry.

The present invention of a microelectronic electroporation array will use a number of different electrode geometries, FIGS. 5A-5D. Four examples of the types of electrode geometries possible with the electroporation array. In FIG. 5A, one unit cell of the array is the cathode 501 and another unit cell is the anode 502. In FIG. 5B, one unit cell is the cathode 503 and 8 others are used as the anode 504. In FIG. 5C, one row 505 is used as the cathode and the adjacent row 506 is used as the anode. In FIG. 5D, the preferred embodiment, a unit cell is used as the cathode 507 and the top of the chamber is used as the anode 508. These are only a few of the geometries possible, others include using multiple unit cells as cathodes and anodes and simultaneously using the top of the chamber as an electrode. The preferred embodiment would have a large plate electrode covering the entire electrode array, FIG. 5D. This would allow for parallel plate electroporation when this is desired. A unit cell or a group of unit cells would be activated to act as either the cathode or the anode and the large plate would be activated to be the opposing electrode. The large plate electrode would be made of a transparent substance to allow for fluorescent imaging of the cells or tissue in culture. Another embodiment will use cathode and anode electrodes that are essentially co-planar. Adjacent unit cells will be used to create an electrical potential gradient sufficient to electroporate cells. The electrodes can be organized into pairs, center surround, parallel columns or other geometries. The advantages of each geometry can be tailored to the individual experiments too be performed. Adjacent pairs, FIG. 5A, of electrodes will allow for the highest number of electroporation sites. Center surround, FIG. 5B, reduces the number of electroporation sites but increases the spatial distribution charges and thus the distribution of pores. Parallel columns allows for gradient experiments. FIG. 5C. Another geometry is to have a wire within the fluid flow chamber act as the opposing electrode. The geometries possible are much greater than electroporation arrays with 1 or a few electrodes.

It is also possible to perform dose response studies of cells to drugs, chemicals or genes, gene silencing RNAi, gene inhibition agents by loading a single concentration of a substance and varying the duration, amplitude or frequency of the applied voltage at different unit cells.

Conducting Electrode Material

Figure 6:
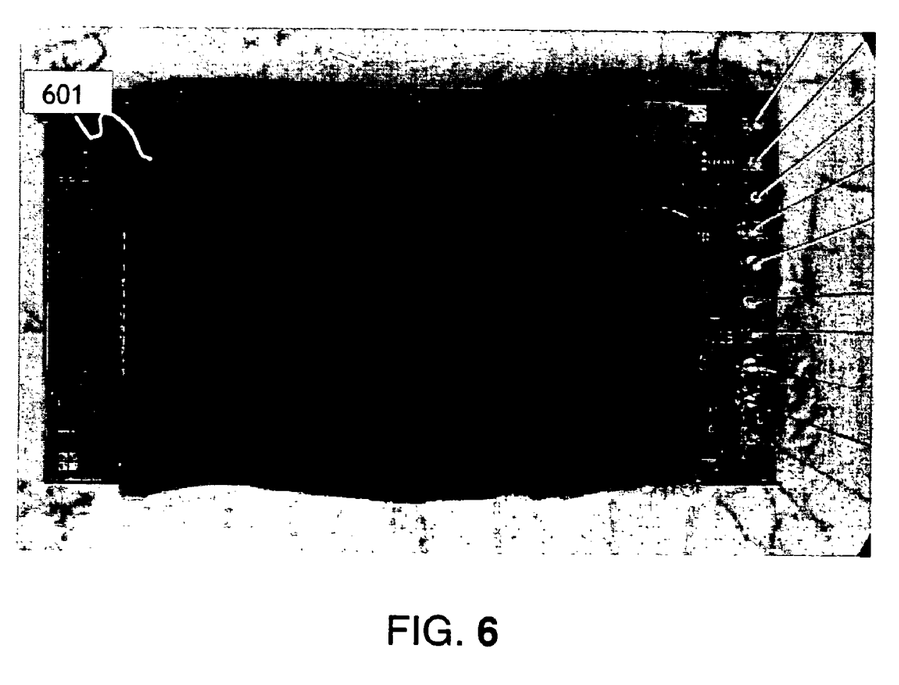
FIG. 6 shows the microwire glass electrode hybridized (attached) to the microelectronic multiplexer.

The cells or lipid vesicles to be electroporated should be grown or cultured in such a way as to plate or deposit them on the surface of the electrodes, preferably in a monolayer. The cells should be cultured using standard cell culture methods for electroporating cells, this requires cell culture media. Cell culture media is a type of saline solution. The silicon multiplexer chip cannot be safely exposed to saline solution. Proper functioning of the device will be maintained if a conducting material is placed on the surface of the chip to protect the chip from saline. It is important that whatever is used as a saline blocker is a good conductor and can retain the independence of each unit cell in the stimulator array. Another problem with the flat vias of the units cell is their relatively high impedance in saline solutions. Still another problem is the potential for cells to be washed away during the filling and washout of the chamber. The preferred embodiment of the electrode surface material is microwire channel glass (MWG) hybridized with indium bump bonds, FIG. 6. MWG electrodes in conjunction with biocompatible epoxy will protect the surface of the silicon chip. The MWG electrode 601 will reduce the impedance by increasing the surface area compared to the flat metal covered vias of silicon chip. The microwires of the MWG electrode act to hold the cells in place during fluid flow. The wires can protrude from the surface of the electrode from zero to several hundred microns. The spaces between the microwires can provide undulations for the cell membranes to sink in. The spaces between the stimulator array and the microwire (glass and the microwires of the microwire glass will be filled in a biocompatible non-conducting epoxy to insulate the unit cells with their bump bonds from one another, provide the cells with a surface compatible with their normal growth and secure the microwire glass electrode to the stimulator array. Excess epoxy can be removed with a suitable method such as plasma etching.

Figure 7:
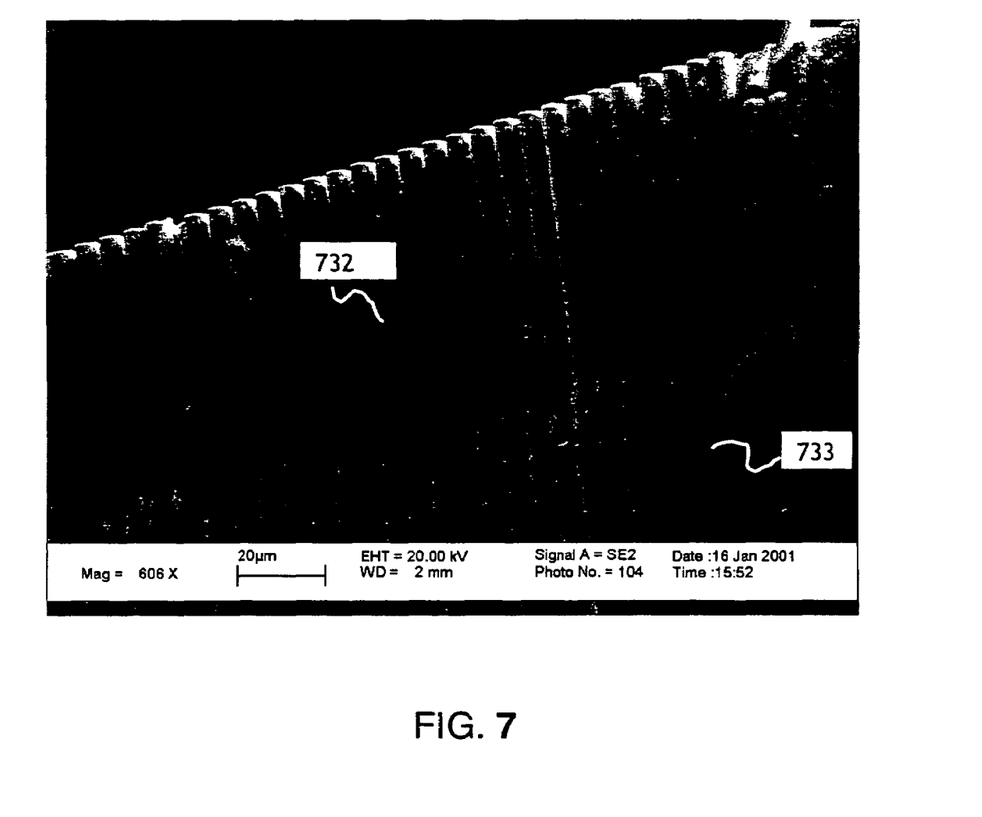
FIG. 7 shows a side view of a microwire glass electrode indication the protruding 6-micron wires.

Channel glass technology employs fiber optic fabrication techniques to produce thin wafers of glass with very small channels perpendicular to the plane of the wafer. Typical channel glass wafers that will be required for the electroporation array are several millimeters in diameter and can contain millions of channels with channel diameters on the order of one micron. The channels are filled with a good electrical conductor. The electrical conductors on the surface should protrude slightly to form efficient electrodes. FIG. 7 shows an image of the channel glass electrode. The view is from the side. The microwires 732 can be seen protruding from the glass matrix 733. The 20 micron scale bar is at the bottom of the image. Multiple microwire connect to each unit cell via of the stimulator chip.

Other embodiments of the electrode surface material include a simple layer of insulating and saline protecting material, which can be photo degraded and cleaned off the of metal vias. The metal vias could be coated with platinum black to improve surface area related impedance and provide a rough surface to help with cell immobilization.

Fluid Flow Chamber and Apparatus

The fluid flow apparatus is designed to perfuse the cells with media or solutions, which maintain the health of the cells or tissue in culture, make available substances to be introduced into the cells via electroporation and efficiently wash away the current medium in preparation for the next substance. The fluid flow apparatus consists of a pump to drive the solution wells, a series of valves to admit or exclude solution from entering the electroporation chamber, an electroporation chamber, and exit valve to prevent reentry of the washout. During the wash out phase, the valve controlling solution entry into the inclination chamber will switch to allow the wash out solution to pass through. The wash out solution may contain chemical attractants for the specific substance being studied.

The electroporation chamber will be a chamber with sidewalls and a transparent top. The transparent top is required for imaging the cell status and function with optical markers. The sidewalls will have an in flow port and an outflow port. In the preferred embodiment, the sidewalls of the chamber will rest on the microwire glass electrode or surrounding epoxy. In the preferred embodiment, the top will consist of a glass slide coverslip adhered to the sides of the chamber. In another embodiment the top is an indium tin oxide coated coverslip to act as a return electrode. In another embodiment the top comprises a piece of glass smaller than a microscope coverslip. In another embodiment the top is made of plastic. In another embodiment the sides rest on a bottom material and the stimulator array and the microwire glass are enclosed within the chamber.

In one embodiment of the device a plastic tube could be pre-filled with the thousands of gene solutions to be studied separated by air and an appropriate volume of washout solution. The tube would then be attached to the fluid flow chamber and the tube contents pumped into the chamber in steps timed with the electroporation of separate unit cells/electrodes of the chip.

To screen thousands of modified genes, gene silencing RNAi, gene inhibition agents, it will be necessary to produce these genes, gene silencing RNAi, gene inhibition agents. Current methods of building custom genes, gene silencing RNAi, gene inhibition agents are relatively costly. Also the concentration of the genes, gene silencing RNAi, gene inhibition agents must be high in order to obtain a reasonable insertion yield. Therefore, the volume of gene solution must be minimized. A great advantage of the microelectronic electroporation array is the small volume of the electroporation chamber. The fact that the cells are not in suspension means the gene solution need not be diluted further by the suspension solution and that only a small volume of gene solution need be passed over the cells. The dimensions of the chamber of the current prototype is 0.1 mm×3 mm×8 mm in height, width and length. The resulting 1.8 mm$^3$, 1.8 µl, is a volume much less than the 15-25 µl to be used in the smallest 384 well plates. The type of plates planned to be used in the device described in U.S. Pat. No. 6,352,853. Other existing array electroporation techniques require at least 50-100 µl.

When cells are plated onto a culture dish, often substances such as polylysine are used to promote adhesion to the surface and improve the strength of the cells culture. These types of substances will be useful in optimizing the present invention. The use of cell adhesion substances will improve viability and stability of the cells under large amount of fast fluid exchange required to repeatedly fill and washout solutions carrying the genes, gene silencing RNAi, gene inhibition agents, drugs or chemicals to be electroporated into the cells. The MWG electrode described above is in part a component of the fluid flow apparatus. The MWG acts to hold the cells in place.

Other substances can be used to promote the formation of monolayers. It will be useful to have monolayers of cells to improve the imaging of the cell culture for various assays. Fluorescent assays of cell function and survival, as well as imaging of fluorescent reporter molecules and genes, gene silencing RNAi, gene inhibition agents will be easier with a monolayer. Furthermore, multiple layers of cells can decrease the amount of gene, drug or chemicals that can come in contact with the cells.

ADVANTAGES

An advantage of the microelectronic electroporation array is the ability to study interactions between cells loaded with different genes, gene silencing RNAi, gene inhibition agents. Unlike standard electroporation methods in which all the cells suspended in a solution or tissue region are electroporated, our method allow subpopulations of cells to be loaded with one gene and other subpopulations to be loaded with a different gene. The additional step of mixing the cells that would be required with existing techniques is eliminated.

Our method would use small metal electrodes on a microchip to electroporate. This is similar to the methods described in papers by Lin et al. 2001 and Huang and Rubinsky. 1999. The primary difference is the use of a multiplexer to allow for thousands of independent electrodes. In addition the present invention is based on a silicon chip, which can be manufactured using standard methods. Also, the devices described in the papers above do not detail technologies or methods to flow fluid across the cells or electrodes designed to hold the cells in place.

The primary advantage of the present invention is the ability to perform high throughput screening of thousands of genes, gene silencing RNAi, gene inhibition agents, drugs or other substances in parallel. This advantage is most clear when the fact that screening gene mutations may require the study of more than 10000 genes, gene silencing RNAi, gene inhibition agents and that current methods allow for the study of only individual genes, gene silencing RNAi, gene inhibition agents or a few hundred genes, gene silencing RNAi, gene inhibition agents at one time. Furthermore, the combinatorial nature of gene, drug or protein formation requires high throughput screening to prevent costs from eclipsing potential returns.

There are a number of reasons why this is important. One reason is the reduction in time to image the resulting optical changes that might be used to assay cell status. One microscope/camera system can image thousands of experiments at once. This is an improvement on the requirement of 96 well plate electroporation arrays to either move the array or used 96 imaging system to assay the optical signal.

The invention claimed is:

1. An electroporation device, comprising:
   an electronic array containing a plurality of circuits forming a 2D array of unit cells;
   a conducting electrode material having a first side in electrical contact with the 2D array of unit cells of the electronic array and a second side opposite the first side, wherein the second side of the conducting electrode material comprises a microfiber glass that is suitable for plating and holding a monolayer of cells or lipid vehicles to be electroporated and wherein the conducting electrode material is selectively conducting such that each of the unit cells of the electronic array is independently conductive therethrough; and
   a fluid flow chamber configured to perfuse the cells or lipid vehicles with a plurality of solutions defined by the second side of the conducting electrode material, a top disposed opposite the second side of the conducting electrode material and at least one sidewall separating the second side of the conducting electrode material and the top, wherein the top comprises an optical window.

2. The device of claim 1, wherein a first selective portion of the conducting electrode material operates as at least one anode and second selective portion of the conducting electrode material operates as at least one diode.

3. The device of claim 2, wherein the first selective portion and the second selective portion are disposed in a geometry selected from a group comprising pairs, center surround, and parallel columns.

4. The device of claim 3, wherein the first selective portion and the second selective portion are repeated in an array across the conducting electrode material.

5. The device of claim 1, wherein at least one selective portion of the conducting electrode material operates as only one of an anode and cathode and wherein the top of the fluid flow chamber includes an opposing electrode.

6. The device of claim 1, wherein the conducting electrode material is connected to the 2D array of unit cells via a plurality of spatially variant indium bumps, each corresponding to one of the 2D array of unit cells.

7. The device of claim 1, wherein the optical window is at least partially transparent.

8. The device of claim 1, wherein the fluid flow chamber comprises a fluid inlet and a fluid outlet.

9. The device of claim 8, wherein the fluid outlet further comprises a valve to prevent back flow.

10. The device of claim 1, further comprising a pump in fluid communication with the fluid flow chamber.

11. The device of claim 1, wherein the electronic array is fabricated on a silicon chip.

12. The device of claim 1, wherein a first selective portion of the conducting electrode material electroporates a first selective area of the monolayer of cells or lipid vesicles and a second selective portion of the conducting electrode material electroporates a second selective area of the monolayer of cells or lipid vesicles.

13. The device of claim 1, wherein the optical window comprises a glass slide coverslip.

14. The device of claim 1, further comprising an optical imaging system configured to image a plurality of cell markers through the optical window.

15. The device of claim 14, wherein the plurality of cell markers comprise cell function and cell status.

16. The device of claim 1, further comprising a tube connected to the fluid flow chamber and configured to store the plurality of solutions, the solutions comprising gene solutions, drug solutions, chemical solutions, and saline solutions.

\* \* \* \* \*